(12) United States Patent
Feijen et al.

(10) Patent No.: US 10,101,677 B2
(45) Date of Patent: Oct. 16, 2018

(54) INSPECTION APPARATUS FOR MEASURING PROPERTIES OF A TARGET STRUCTURE, METHODS OF OPERATING AN OPTICAL SYSTEM, METHOD OF MANUFACTURING DEVICES

(71) Applicant: ASML Netherlands B.V., Veldhoven (NL)

(72) Inventors: Kim Gerard Feijen, Overpelt (BE); Henricus Wilhelmus Maria Van Buel, 's-Hertogenbosch (NL); Martinus Joseph Kok, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/087,299

(22) Filed: Mar. 31, 2016

(65) Prior Publication Data

US 2016/0291479 A1 Oct. 6, 2016

(30) Foreign Application Priority Data

Apr. 3, 2015 (EP) .................................... 15248019

(51) Int. Cl.
*G03F 7/20* (2006.01)
*G03F 9/00* (2006.01)
(Continued)

(52) U.S. Cl.
CPC ........ *G03F 9/7088* (2013.01); *G01B 11/0616* (2013.01); *G01B 11/14* (2013.01);
(Continued)

(58) Field of Classification Search
CPC ... G01B 11/14; G01B 11/272; G01B 11/0616; G01N 21/956; G02B 26/004;
(Continued)

(56) References Cited

U.S. PATENT DOCUMENTS

| 5,033,831 A | 7/1991 | Sigler |
|---|---|---|
| 6,936,809 B2 | 8/2005 | Viinikanoja |

(Continued)

FOREIGN PATENT DOCUMENTS

| JP | H 01227124 A | 9/1989 |
|---|---|---|
| JP | 2006-251343 A | 9/2006 |

(Continued)

OTHER PUBLICATIONS

International Search Report and Written Opinion of the International Searching Authority directed to related International Patent Application No. PCT/EP2016/056870, dated Jul. 21, 2016, 12 pages.

(Continued)

*Primary Examiner* — Michelle M Iacoletti
(74) *Attorney, Agent, or Firm* — Storno, Kessler, Goldstein & Fox P.L.L.C.

(57) ABSTRACT

An inspection apparatus (for example a scatterometer) comprises: a substrate support for supporting a substrate and an optical system. An illumination system illuminates a target (T) with radiation. A positioning system (518) moves one or both of the optical system and the substrate support so as to position an individual target (T) relative to the optical system so that the imaging optics can use a portion of the diffracted radiation to form an image of the target structure on an image sensor (23). A liquid lens (722) is controlled (902) by feed-forward control to maintain said image stationary against vibration and/or scanning movement between the optical system and the target structure. In a second aspect, a liquid lens (1324, 1363) to correct chromatic aberration during measurements made at different wavelengths. This may improve focusing of the illumination on the target (T), and/or focusing of an image on the image sensor (23).

12 Claims, 14 Drawing Sheets

(51) Int. Cl.

| | | |
|---|---|---|
| *G01B 11/06* | (2006.01) | |
| *G01B 11/14* | (2006.01) | |
| *G01B 11/27* | (2006.01) | |
| *G02B 3/14* | (2006.01) | |
| *G02B 26/00* | (2006.01) | |
| *G02B 27/00* | (2006.01) | |
| *G01N 21/956* | (2006.01) | |

(52) U.S. Cl.
CPC ......... *G01B 11/272* (2013.01); *G01N 21/956* (2013.01); *G02B 3/14* (2013.01); *G02B 26/004* (2013.01); *G02B 27/0068* (2013.01); *G03F 7/706* (2013.01); *G03F 7/70683* (2013.01); *G03F 9/7069* (2013.01); *G03F 9/7092* (2013.01)

(58) Field of Classification Search
CPC ....... G02B 27/0068; G02B 3/14; G03F 7/706; G03F 7/70683
See application file for complete search history.

(56) References Cited

U.S. PATENT DOCUMENTS

| | | | |
|---|---|---|---|
| 8,400,558 | B2 | 3/2013 | Berge et al. |
| 8,687,281 | B2 | 4/2014 | Jannard et al. |
| 2005/0225877 | A1 | 10/2005 | Tang |
| 2006/0033921 | A1 | 2/2006 | Den Boef et al. |
| 2006/0066855 | A1 | 3/2006 | Boef et al. |
| 2008/0186482 | A1 | 8/2008 | Den Boef et al. |
| 2010/0201963 | A1 | 8/2010 | Cramer et al. |
| 2010/0328655 | A1 | 12/2010 | Den Boef et al. |
| 2011/0027704 | A1 | 2/2011 | Cramer et al. |
| 2011/0043791 | A1 | 2/2011 | Smilde et al. |
| 2011/0069292 | A1 | 3/2011 | Den Boef |
| 2011/0102753 | A1 | 5/2011 | Van De Kerkhof et al. |
| 2011/0188127 | A1* | 8/2011 | Yamamoto ............... G02B 3/14 359/665 |
| 2012/0044470 | A1 | 2/2012 | Smilde et al. |
| 2012/0123581 | A1 | 5/2012 | Smilde et al. |
| 2012/0127582 | A1* | 5/2012 | Obu ........................ G02B 3/14 359/676 |
| 2013/0070339 | A1 | 3/2013 | Pretorius |
| 2013/0258310 | A1 | 10/2013 | Smilde et al. |
| 2013/0271740 | A1 | 10/2013 | Quintanilha |

FOREIGN PATENT DOCUMENTS

| | | |
|---|---|---|
| TW | 200708759 A | 3/2007 |
| WO | WO 2013/178422 A1 | 12/2013 |

OTHER PUBLICATIONS

"Electrowetting", Varioptic, downloaded Apr. 1, 2015; 3 pages.
"Liquid Lens for Optical Image Stabilization (OIS)", Varioptic, downloaded Feb. 27, 2015; 4 pages.
"The Liquid Lens Technology: How It Works and What It Is Doing", Varioptic (2010), downloaded Feb. 27, 2015; 2 pages.
"What's new in Oto-Rhino Laryngology: LED Headlight KS70", Karl-Storz Endoskope; 2 pages.
Feenstra, J., et al., "Electrowetting displays", Liquavista Electrowetting Displays Whitepaper, (May 2009); 15 pages.
Mugele, F., et al., "Electrowetting: from basics to applications", J. Phys.: Condens. Matter 17 (2005); pp. R705-R774. (submitted in 2 parts).
Simon, E., et al., "Optical image stabilization with a liquid lens", Varioptic, downloaded Feb. 27, 2015; 2 pages.
Xu et al., "A novel adaptive mechanical-wetting lens for visible and near infrared imaging", Optics Express vol. 18, No. 12, (Jun. 7, 2010); pp. 12430-12435.
English-language abstract for App. No. JPH 01227124 A, published Sep. 11, 1989; 2 pages.
English-language abstract for App. No. JP 2006251343 A, published Sep. 21, 2006; 1 page.

\* cited by examiner

INSPECTION APPARATUS FOR MEASURING PROPERTIES OF A TARGET STRUCTURE, METHODS OF OPERATING AN OPTICAL SYSTEM, METHOD OF MANUFACTURING DEVICES

CROSS REFERENCE TO RELATED APPLICATIONS

This application claims benefit to EP Application 15248019.0, which is incorporated by reference herein in its entirety.

BACKGROUND

Field of the Invention

The present invention relates to inspection apparatus for measuring properties of a target structure on a substrate, and to methods of operating optical systems such as inspection apparatuses.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a diffraction "spectrum" from which a property of interest of the target can be determined.

Examples of known scatterometers include angle-resolved scatterometers of the type described in US2006033921A1 and US2010201963A1. The targets used by such scatterometers are relatively large, e.g., 40 µm by 40 µm, gratings and the measurement beam generates a spot that is smaller than the grating (i.e., the grating is underfilled). In addition to measurement of feature shapes by reconstruction, diffraction based overlay can be measured using such apparatus, as described in published patent application US2006066855A1. Diffraction-based overlay metrology using dark-field imaging of the diffraction orders enables overlay measurements on smaller targets. Examples of dark field imaging metrology can be found in international patent applications US20100328655A1 and US2011069292A1 which documents are hereby incorporated by reference in their entirety. Further developments of the technique have been described in published patent publications US20110027704A, US20110043791A, US2011102753A1, US20120044470A, US20120123581A, US20130258310A, US20130271740A and WO2013178422A1. These targets can be smaller than the illumination spot and may be surrounded by product structures on a wafer. Multiple gratings can be measured in one image, using a composite grating target. The contents of all these applications are also incorporated herein by reference.

In order to measure targets at different locations across a substrate, the known scatterometers include a positioning system for moving the substrate and a measurement optical system relative to one another. The relative movement may be achieved by moving the substrate while the optical system remains stationary, by moving the optical system while the substrate remains stationary, or by moving both the substrate and the optical system. In a known example, the substrate is moved in one dimension (for example, an X direction) while the optical system moves in another direction (for example, Y). In any of these systems, it is necessary for the moving parts to come to a standstill before an accurate measurement can be made. The settling time involved in this adds to the overall measurement time, and reduces the number of measurements that can be made in a given time interval.

The known scatterometers include an illumination system for forming a spot of radiation to be used in making measurements. The inspection apparatus includes an illumination system comprising one or more radiation sources and an illumination optical system (illumination optics) for the delivery of the illumination with the desired illumination parameters. In practice, it will be desired that the illumination system can switch between different wavelengths of illumination between measurements. In the following, the term 'light' will be used for convenience to refer the illuminating radiation, without implying any limitation to visible wavelengths. Different wavelengths of light experience different refractive indices in an optical system. Even though measures may be taken to reduce this so-called 'chromatic aberration', the measurements can be undesirably different at different wavelengths.

SUMMARY OF THE INVENTION

The present disclosure in some aspects aims to provide improved measurement performance and/or improved throughput of measurements in an inspection apparatus such as for example a scatterometer including an imaging optical system.

The present disclosure in a first aspect provides an inspection apparatus for measuring properties of a target structure on a substrate, the apparatus comprising:

a substrate support for supporting the substrate;

an optical system for illuminating the target structure with radiation and collecting diffracted radiation from the target structure, the optical system comprising imaging optics and an image sensor; and a positioning system for causing movements of one or both of the optical system and the substrate support so as to position an individual target structure relative to the optical system so that the imaging optics can use a portion of the diffracted radiation to form an image of the target structure on the image sensor during an image acquisition interval, wherein the imaging optics includes a liquid lens and a controller, the controller being operable to control the liquid lens to maintain said image stationary during said image acquisition interval while allowing for relative movement between the optical system and the target structure.

The provision of the liquid lens can be exploited in various ways. The liquid lens can used to allow image acquisition to begin without waiting for the apparatus to settle after a movement. Throughput may be improved.

The liquid lens can also be used to compensate a scanning movement so that movement of the optical system and/or the substrate does not need to stop at all. By acquiring an image during a scanning movement, position-dependent aberrations in the optical system can be averaged out and accuracy of measurement can be improved. Throughput may be improved.

The disclosure in a second aspect provides inspection apparatus for measuring properties of a target structure on a substrate, the apparatus comprising:

an optical system for illuminating a target structure with radiation and collecting diffracted radiation from the target structure, the optical system including illumination optics, imaging optics and an image sensor, the imaging optics using a portion of the diffracted radiation to form an image of the target structure on the image sensor;

wherein the optical system is arranged to illuminate the target structure and form an image while selecting a wavelength range of said radiation, and wherein the imaging subsystem comprises a liquid lens and a controller, the controller being operable to control the liquid lens to compensate for chromatic aberration of the of the optical system according to the selected wavelength range.

There are further disclosed methods of operating optical systems such as an inspection apparatus using one or more liquid lenses.

There is further disclosed a method of manufacturing devices using measurements made by an inspection apparatus or method as set forth above.

The invention yet further provides a computer program product comprising machine-readable instructions for causing a programmable controller to implement methods according to the various aspects of the disclosure set forth above. The instructions may be stored in a non-transient storage medium.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
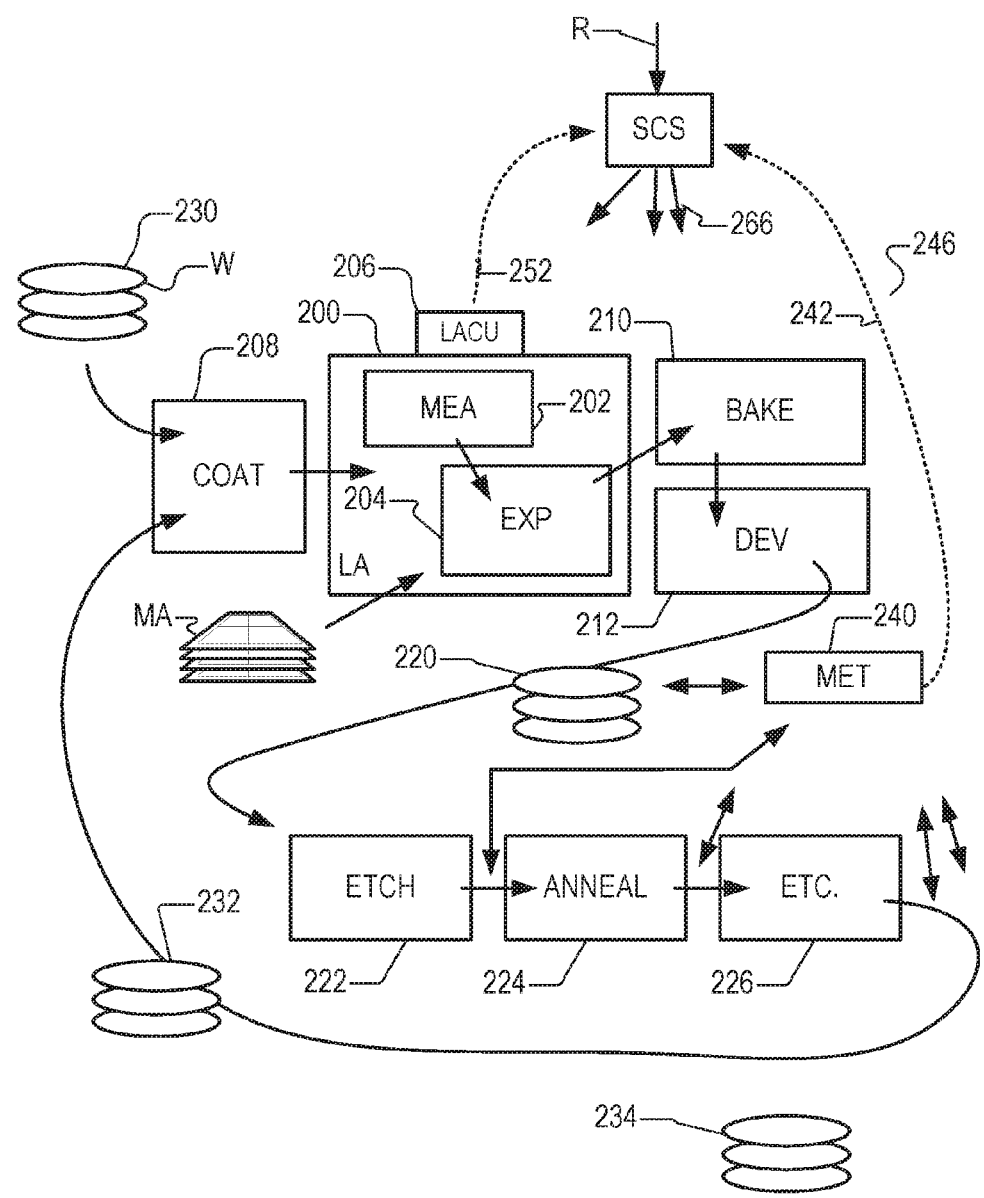
FIG. 1 is a schematic depiction of an industrial production facility including a lithographic apparatus LA and an inspection apparatus MET among other apparatuses.

FIG. 1 at 200 shows a lithographic apparatus LA as part of an industrial production facility implementing a high-volume, lithographic manufacturing process. In the present example, the manufacturing process is adapted for the manufacture of for semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables WTa and WTb and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes one or more pieces of inspection apparatus which receive some or all of the substrates W that have been processed in the litho cell.

For example, the system shown in FIG. 1 includes an inspection apparatus in the form of metrology apparatus 240, which is provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 220 prior to etching in the apparatus 222. Using metrology apparatus 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, metrology apparatus 240 and/or other metrology apparatuses (not shown) can be applied to measure properties of the processed substrates 232, 234, and incoming substrates 230.

Other types of inspection apparatus are known, for example for defect detection.

Figure 2A:
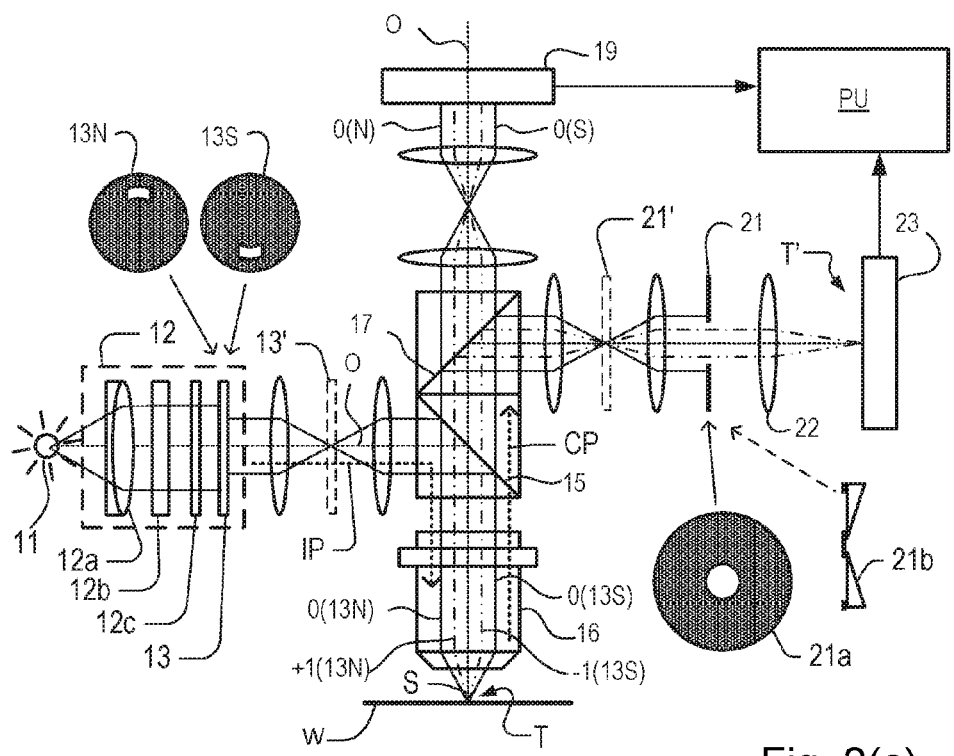
FIGS. 2(a) and 2(b) depict a known form of scatterometer usable as the inspection apparatus in the production facility of FIG. 1.

FIG. 2(a) shows an inspection apparatus implementing angle-resolved scatterometry with adaptations for performing so-called dark field imaging. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating T and diffracted rays are illustrated in more detail in FIG. 2(b).

In this type of inspection apparatus, radiation emitted by a radiation source 11 is conditioned by an illumination system 12. For example, illumination system 12 may include a collimating using lens system 12a, a color filter 12b, a polarizer 12c and an aperture device 13. The conditioned radiation follows an illumination path IP, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures greater than 1, if desired.

As in the lithographic apparatus LA, one or more substrate supports may be provided to hold the substrate W during measurement operations. Coarse and fine positioners may be configured to accurately position the substrate in relation to a measurement optical system. Various sensors and actuators are provided for example to acquire the position of a target of interest, and to bring it into position under the objective lens 16. Typically many measurements will be made on targets at different locations across substrate W. The substrate support can be moved in X and Y directions to acquire different targets, and in the Z direction to obtain a desired focusing of the optical system on the target. However, it is of course equally possible to have the optical system move and the substrate table be stationary. Further, it is equally possible to have the optical system move in one cardinal direction (such as the Y direction) and the substrate table move in the other cardinal directions (such as the X and Z directions).

From the point of view of the user of the measurements, provided the relative position of the substrate and the optical system is correct, it does not matter in principle whether one or both of those is moving in the real world. It is convenient simply to think and describe operations as if the objective lens and optical system being brought to different locations on the substrate. For the practical implementation of the apparatus, however, there are important advantages and drawbacks to each choice. For example, it has been found that a compact arrangement can be achieved by having the optical system move in one direction while the substrate support moves in the other direction. Movement of the optical system brings challenges with management of vibrations, for example.

Radiation reflected by the substrate, including radiation diffracted by any metrology target T, is collected by lens 16 and follows a collection path CP in which it passes through partially reflecting surface 15 into a detector 19. The detector may be located in the back-projected pupil plane P, which is at the focal length F of the lens 16. In practice, the pupil plane itself may be inaccessible, and may instead be re-imaged with auxiliary optics (not shown) onto the detector located in a so-called conjugate pupil plane P'. The detector is preferably a two-dimensional detector so that a two-dimensional angular scatter spectrum or diffraction spectrum of a substrate target 30 can be measured. In the pupil plane or conjugate pupil plane, the radial position of radiation defines the angle of incidence/departure of the radiation in the plane of focused spot S, and the angular position around an optical axis O defines azimuth angle of the radiation. The detector 19 may be, for example, an array of CCD or CMOS sensors, and may use an integration time of, for example, 40 milliseconds per frame.

Radiation in reference path RP is projected onto a different part of the same detector 19 or alternatively on to a different detector (not shown). A reference beam is often used for example to measure the intensity of the incident radiation, to allow normalization of the intensity values measured in the scatter spectrum.

The various components of illumination system 12 can be adjustable to implement different metrology 'recipes' within the same apparatus. Color filter 12b may be implemented for example by a set of interference filters to select different wavelengths of interest in the range of, say, 405-790 nm or even lower, such as 200-300 nm. An interference filter may be tunable rather than comprising a set of different filters. A grating could be used instead of interference filters. Alternatively or in addition, wavelengths can be changed within source 11, or by swapping sources. Polarizer 12c may be rotatable or swappable so as to implement different polarization states in the radiation spot S. Aperture device 13 can be adjusted to implement different illumination profiles. Aperture device 13 is located in a plane P" conjugate with pupil plane P of objective lens 16 and the plane of the detector 19. In this way, an illumination profile defined by the aperture device defines the angular distribution of light incident on substrate radiation passing through different locations on aperture device 13.

The detector 19 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PS. Illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

Figure 3:
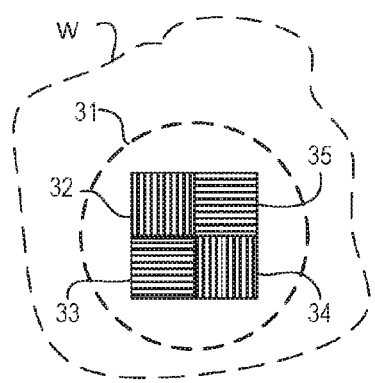
FIG. 3 depicts a known form of multiple grating target and an outline of a measurement spot on a substrate.
Figure 4:
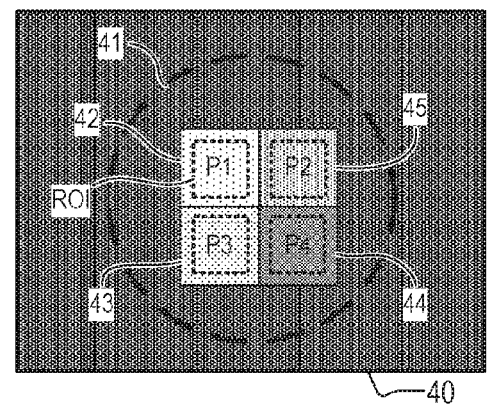
FIG. 4 depicts an image of the target of FIG. 3 obtained in the scatterometer of FIG. 2.

In addition to measurement of parameters by reconstruction, angle resolved scatterometry is useful in the measurement of asymmetry of features in product and/or resist patterns. A particular application of asymmetry measurement is for the measurement of overlay, where the target comprises one set of periodic features superimposed on another. The concepts of asymmetry measurement using the instrument of FIG. 3 or 4 are described for example in published patent application US2006066855A1 cited above. Simply stated, while the positions of the diffraction orders in the diffraction spectrum of the target are determined only by the periodicity of the target, asymmetry of intensity levels in the diffraction spectrum is indicative of asymmetry in the individual features which make up the target. In the instrument of FIG. 4, where detector 19 may be an image sensor, such asymmetry in the diffraction orders appears directly as asymmetry in the pupil image recorded by detector 19. This asymmetry can be measured by digital image processing in unit PU, and calibrated against known values of overlay.

In the second measurement branch, imaging optical system 22 forms an image of the target on the substrate W on sensor 23 (e.g. a CCD or CMOS sensor). An aperture stop 21 is provided in a plane that is in the collection path in a plane conjugate to the pupil-plane (it may also be called a pupil stop). Aperture stop 21 can take different forms, just as the illumination aperture can take different forms. Examples 21a and 21b will be discussed below. Typically, aperture stop 21 functions to block the zeroth order diffracted beam so that the image of the target formed on sensor 23 is formed only from the first order beam(s). This is the so-called dark field image, equivalent to dark field microscopy. The images captured by sensors 19 and 23 are output to image processor and controller PU, the function of which will depend on the particular type of measurements being performed.

In the illumination path in this example, additional optics are shown such that a field stop 13' can be placed in a plane conjugate with the plane of the target and the image sensor 23. This plane may be referred to as a field plane, or conjugate image plane, and has the property that each spatial position across the field plane corresponds to a position across the target. This field stop may be used for example to shape the illumination spot for a particular purpose, or simply to avoid illuminating features that are within the field of view of the apparatus but not part of the target of interest. The following drawings and discussion refer, by way of example, to techniques for implementation of the function of aperture device 13, but the present disclosure also encompasses use of the same techniques to implement the function of field stop 13'.

Figure 2B:
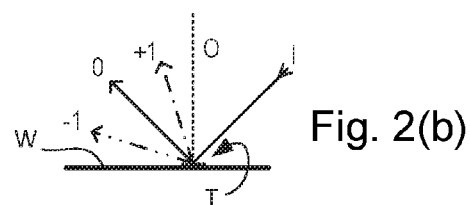

As shown in more detail in FIG. 2(b), target grating T is placed with substrate W normal to the optical axis O of objective lens 16. In the case of an off-axis illumination profile, A ray of illumination I impinging on grating T from an angle off the axis O gives rise to a zeroth order ray (solid line O) and two first order rays (dot-chain line +1 and double dot-chain line −1). It should be remembered that with an overfilled small target grating, these rays are just one of many parallel rays covering the area of the substrate including metrology target grating T and other features. Since the annular aperture 13a in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

Other modes of illumination are possible by using different apertures. For example, aperture 13b provides on-axis illumination. Apertures 13N (north') and 13S (south') each provide off-axis illumination from a specific narrow range of angles only. Returning to FIG. 2(a), this is illustrated by designating diametrically opposite portions of the annular aperture as north (N) and south (S). The +1 diffracted rays from the north portion of the cone of illumination, which are labeled +1(13N), enter the objective lens 16, and so do the −1 diffracted rays from the south portion of the cone (labeled −1(13S)). As described in the prior applications mentioned in the introduction, using the dark-field imaging senor 23 while switching between apertures 13N, 13S of this type is one way of obtaining asymmetry measurements from multiple small targets. Aperture stop 21a can be used to block the zeroth order radiation when using off-axis illumination.

While off-axis illumination is shown, on-axis illumination of the targets may instead be used and an aperture stop 13b with an off-axis aperture is used to pass substantially only one first order of diffracted light to the sensor. In one example, prisms 21b are used in place of aperture stop 21 which have the effect of diverting the +1 and −1 orders to different locations on sensor 23 so that they can be detected and compared without making two images. This technique is disclosed in the above-mentioned published patent application US2011102753A1, the contents of which are hereby incorporated by reference. 2nd, 3rd and higher order beams (not shown in FIG. 2) can be used in measurements, instead of or in addition to the first order beams.

FIG. 3 depicts a composite grating target formed on a substrate according to known practice. The composite target comprises four individual gratings 32 to 35 positioned closely together so that they will all be within a measurement spot 31 formed by the illumination beam of the metrology apparatus. The four targets thus are all simultaneously illuminated and simultaneously imaged on sensors 19 and 23. In an example dedicated to overlay measurement, gratings 32 to 35 are themselves composite gratings formed by overlying gratings that are patterned in different layers of the semiconductor device formed on substrate W. Gratings 32 to 35 may have differently biased overlay offsets in order to facilitate measurement of overlay between the layers in which the different parts of the composite gratings are formed. Gratings 32 to 35 may also differ in their orientation, as shown, so as to diffract incoming radiation in X and Y directions. In one example, gratings 32 and 34 are X-direction gratings with biases of the +d, −d, respectively. This means that grating 32 has its overlying components arranged so that if they were both printed exactly at their nominal locations one of the components would be offset relative to the other by a distance d. Grating 34 has its components arranged so that if perfectly printed there would be an offset of d but in the opposite direction to the first grating and so on. Gratings 33 and 35 are Y-direction gratings with offsets +d and −d respectively. While four gratings are illustrated, another embodiment might require a larger matrix to obtain the desired accuracy. For example, a 3×3 array of nine composite gratings may have biases −4d, −3d, −2d, −d, 0, +d, +2d, +3d, +4d. Separate images of these gratings can be identified in the image captured by sensor 23.

FIG. 4 shows an example of an image that may be formed on and detected by the sensor 23, using the target of FIG. 3 in the apparatus of FIG. 2. While the pupil plane image sensor 19 cannot resolve the different individual gratings 32 to 35, the image sensor 23 can do so. The cross-hatched rectangle 40 represents the field of the image on the sensor, within which the illuminated spot 31 on the substrate is imaged into a corresponding circular area 41. Ideally the field is dark. Within this dark field image, rectangular areas 42-45 represent the images of the individual gratings 32 to 35. If the gratings are located in product areas, product features may also be visible in the periphery of this image field. While only a single composite grating target is shown in the dark field image of FIG. 5, in practice a semiconductor device or other product made by lithography may have many layers, and overlay measurements are desired to be made between different pairs of layers. For each overlay measurement between pair of layers, one or more composite grating targets are required, and therefore other composite grating targets may be present, within the image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole. However the need for accurate alignment remains if the imaging process is subject to non-uniformities across the image field. In one embodiment of the invention, four positions P1 to P4 are identified and the gratings are aligned as much as possible with these known positions.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter.

Figure 5:
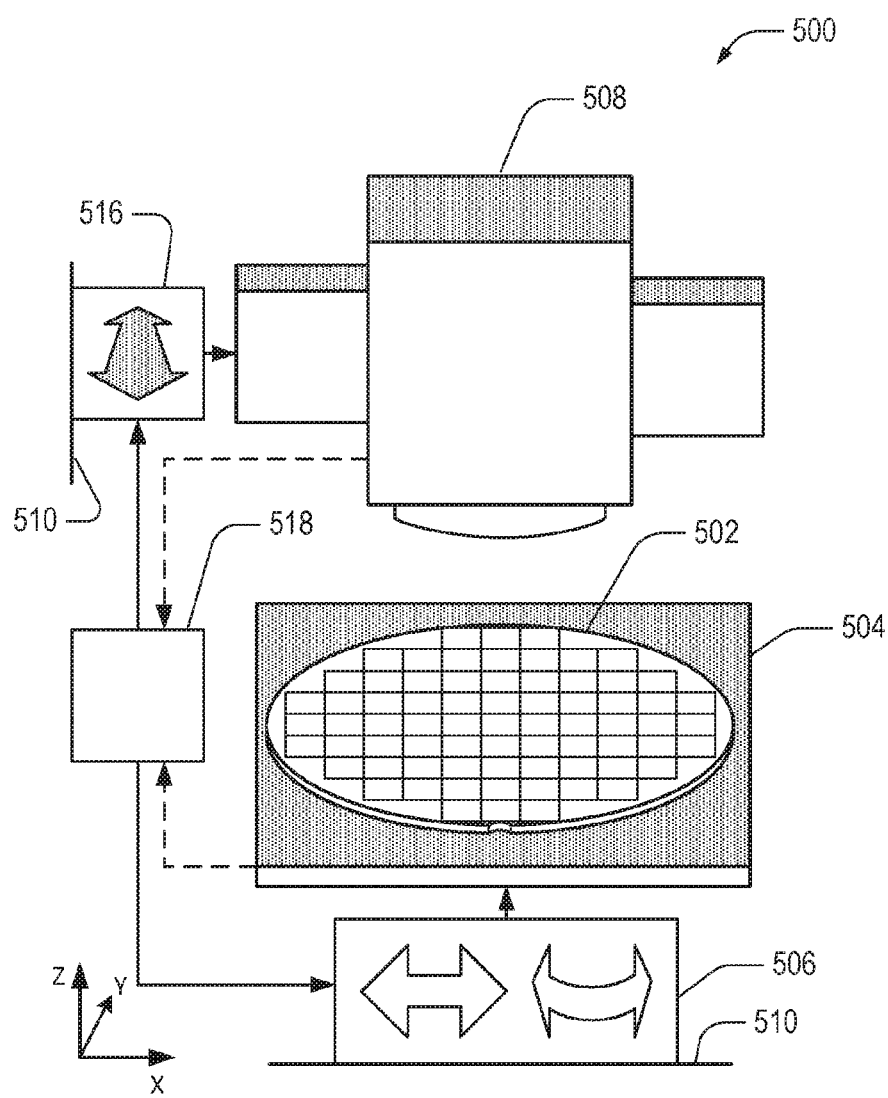
FIG. 5 illustrates schematically movements of parts of the inspection apparatus for the measurement of different targets on a substrate.

FIG. 5 shows schematically a positioning system in an inspection apparatus 500 according to one particular example. A substrate 502 is placed on a substrate support 504. The substrate support has a set of actuators 506, which are able to move the substrate support in the X direction, as well as able to rotate the substrate support around the Z axis.

An optical system of the inspection apparatus, which may be the same as that discussed with reference to FIG. 2, is contained generally within a housing 508. Different portions of the housing may contain a light source, illumination system, imaging optical system and one or more image detectors. The optical system housing 508 is attached to a frame 510, which serves as a fixed reference for both the optical system and the substrate support. An actuator 516 is provided to move the optical system back and forth in the Y direction.

The actuators 506, 516 of the optical system and the substrate support are controlled by a controller 518, and together with the frame 510 these form a positioning system. The positioning system controls the relative positions of the optical system and the substrate support based on position information. Such information can be determined in a number of ways. One or both of the optical system and the substrate support may be fitted with position sensors (not shown), which transmit positional data 520, 522 directly to the controller 518. Alternatively or additionally, position information can be entered manually by a user, or can be transmitted from remotely located sensors. It will be appreciated that the positioning system is illustrated in a highly simplified form. In practice, each actuator may be divided into coarse and fine stages, sometimes called 'long throw' and 'short throw' actuators. Controller 518 may be implemented in a distributed fashion, with for example a short-throw actuator having its own local controller to form a subsystem of the overall positioning system. These implementational details are a matter of routine design for the skilled reader.

Figure 6:
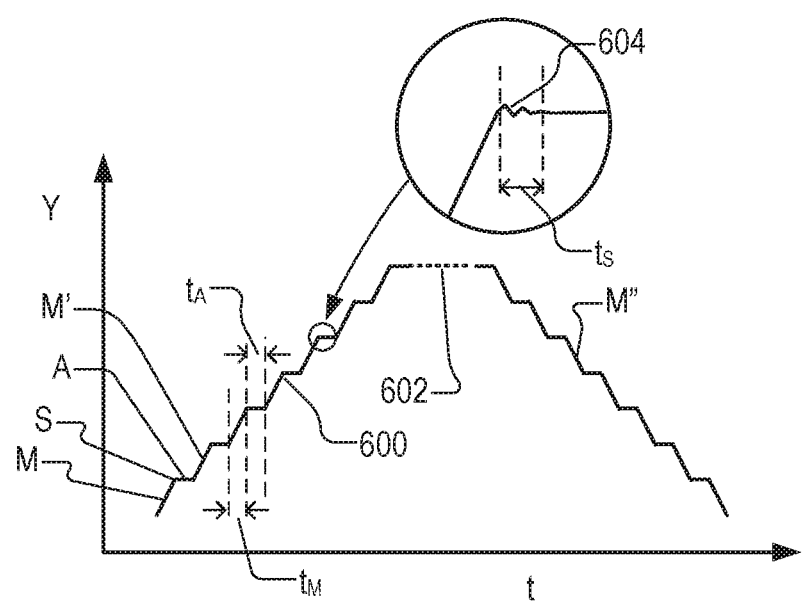
FIG. 6 is a graph showing one component of movement in the apparatus of FIG. 5 during a series of measurements.

Referring to FIG. 6, the graph illustrates a problem that may arise during operation of the inspection apparatus. Supposing that the optical system in housing 508 is being used to measure properties of a substrate using the imaging optical system 22 and image sensor 23. The trace 600 shows the position Y of the optical system varying over time t. To acquire a series of targets, controller 218 and actuator 216 perform a sequence of moves and stops, as shown. A move M is followed by a stop S and a period of holding A while an image is acquired. Then a next move M' takes the optical system to the next target. Moves in the X direction may be performed simultaneously with the Y moves shown. At 602, processing is interrupted (for example to perform a Y move, and/or to change an illumination mode and/or to swap in a new substrate), and a new sequence of move-stop-hold-move is begun (M'').

In an ideal world, the time taken for a number of measurements would depend simply on the total of movement times tM and acquisition times tA. As indicated in the inset detail, however, the mechanical system needs a settling time tS after the movement, before all components are still enough to acquire an image of a particular target area on the substrate. After any moving part stops movement, there will be transient relative movement 604 between the optical system and the substrate support. This transient movement is in part caused by vibrations caused by the actuation of the various parts of the inspection apparatus, and is in part caused by the momentum of the moving parts. The transient movement negatively influences the quality of any images taken by the image detector. It is therefore necessary to wait for a settling time tS until the transient movement has subsided below a particular threshold before acquiring images. Image acquisition then takes another period of time. The need for settling time slows down measurement speed, and therefore throughput of the inspection apparatus.

Figure 7:
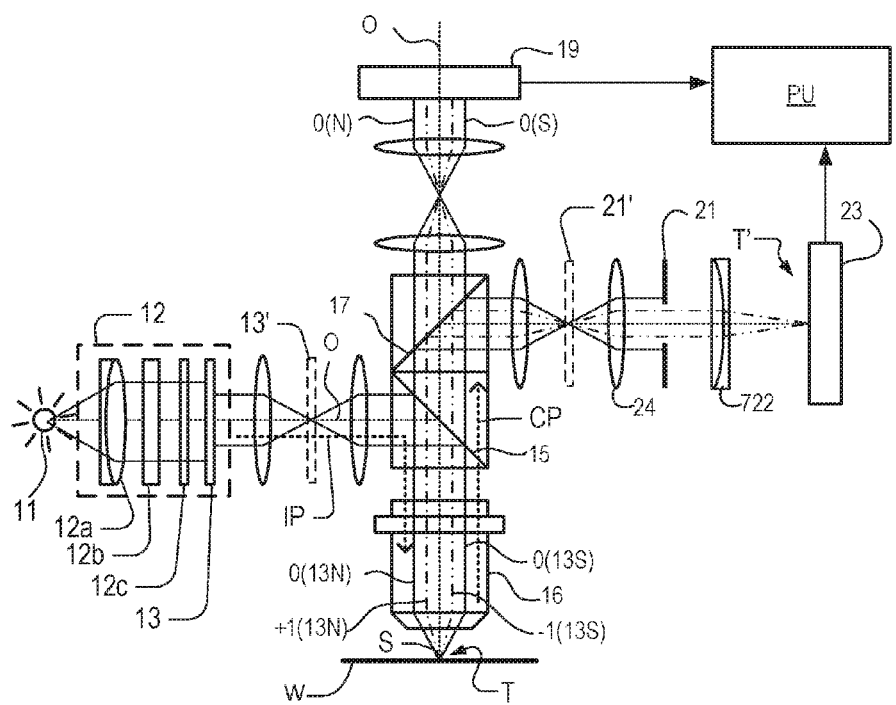
FIG. 7 shows a first modified inspection apparatus incorporating a liquid lens in an imaging optical system according to one aspect of the present disclosure.

FIG. 7 shows modified inspection apparatus according to a first aspect of the present disclosure. The inspection apparatus is identical to that of FIG. 2, except that a lens 22 in the imaging optical system has been replaced by a liquid lens 722. FIG. 8 shows a schematic cross-sectional view of a liquid lens 800, suitable for use as lens 722 in the apparatus of FIG. 7. The liquid lens has a first surface 802 and a second surface 804. Between the surfaces, there is contained a first liquid 806 with a first refractive index and a second liquid 808 with a second refractive index. The liquids are not miscible, and therefore maintain a defined interface 809 with different refractive indices on either side. For example, the first liquid could be water-based and the second liquid could be oil-based. First and second electrodes 810, 812 are placed in the side walls of the liquid lens. It is to be noted that, while only two electrodes are shown in the Figure, the lens 800 has a number of electrodes arranged around its periphery. The water-based liquid can be attracted or repelled by the electrode, by the phenomenon known as 'electro wetting'. When voltage is applied to the electrodes, the interface between the liquids will form a particular shape that is dependent on the voltages applied to the electrodes.

Figure 8A:
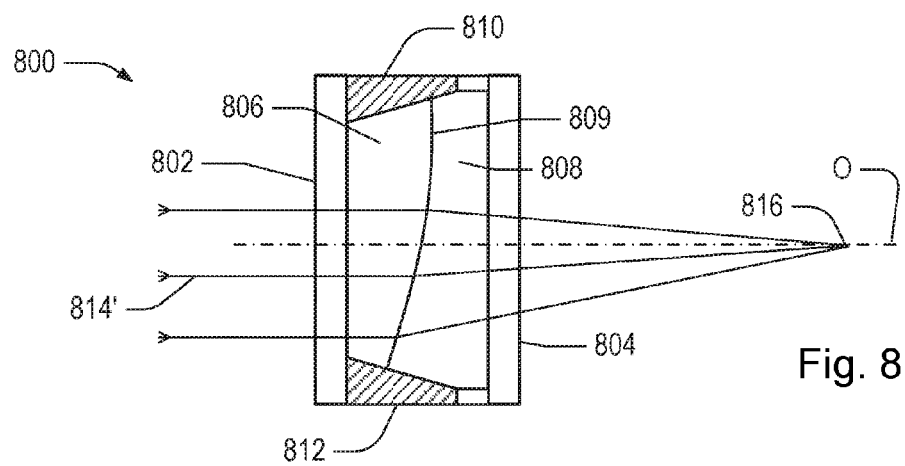
FIGS. 8(a)-8(c) show the working principle of a multi-pole liquid lens used in the modified inspection apparatus of FIG. 7.
Figure 8B:
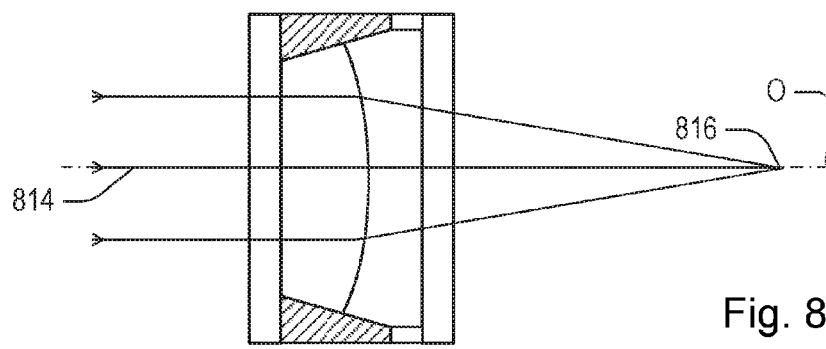

FIG. 8 shows different shapes (a), (b), (c) that can be achieved in the interface 809 between liquids, by suitable control of the electrode voltages. When the voltages applied to all of the electrodes are identical, a curved interface 809 will be formed which is symmetrical about an optical axis O, as shown in FIG. 8(b). In this situation, the liquid lens will act as a normal lens, i.e. it will focus the light which enters at a given focal distance dependent on the curvature of the lens surface. By increasing the voltage applied to the electrodes, the curvature of the lens surface can be changed, which permits the focal length of the liquid lens to be changed accordingly. It is worth noting that a liquid lens can also be used as a diverging lens by appropriate application of currents to the electrodes.

Figure 8C:
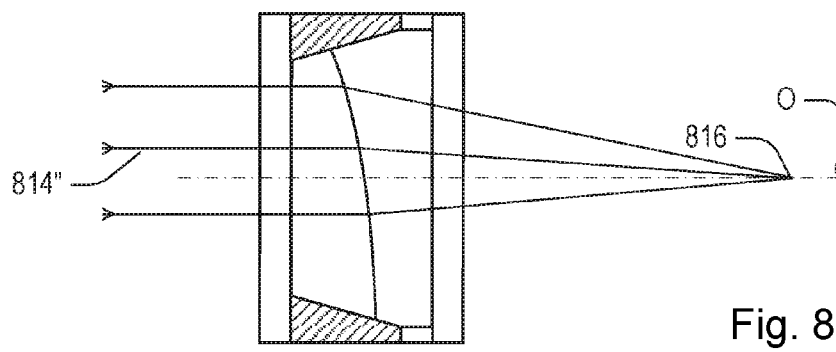

If different voltages are applied to the different electrodes, the shape of interface 809 will no longer be symmetrical about the optical axis. FIGS. 8(a) and 8(c) illustrate situations where the lens interface is shaped so as to have an off-axis focal point. In the context of its application in the apparatus of FIG. 8, rays 814, 814' and 814" from different positions in an incoming light field, can be focused at a desired point 816, by controlling the voltages applied to the electrodes.

It is to be noted that a liquid lens can, of course, have any convenient number of electrodes. A higher number of electrodes will enable a more precise control over the surface shape of the first liquid, and hence allow more precise and/or specific control over the characteristics of the liquid lens. Eight electrodes may be used, for example.

FIG. 9 illustrates how the liquid lens 722 in the apparatus of FIG. 7 can be used to improve imaging performance and/or throughput, compared with the conventional apparatus of FIG. 2. The optical system of the apparatus is illustrated in a simplified form, highlighting the objective lens 16, the lens 22/722 of the imaging optical system and the image sensor 23.

The positioning system (FIG. 5) is represented schematically in FIG. 9 by the controller 518, with associated command lines and sensor data lines. Within the positioning system, controller 518 sends commands to actuators 506 in order to position the substrate support and substrate correctly in relation to frame 510. The position sensors on the substrate support transmit position data back to the position controller. Within the positioning system, controller 518 sends commands to actuators 516 in order to position the optical system correctly in relation to frame 510. Similarly to the substrate stage, the optical system has one or more position sensors, which transmit position data back to the position controller. This allows controller 518 to determine of positional deviations, for example due to vibrations or outside influences in the inspection apparatus. Appropriate corrections are then commanded, to implement one or more servo control loops. Other sensors, such as accelerometers may be provided.

Figure 9A:
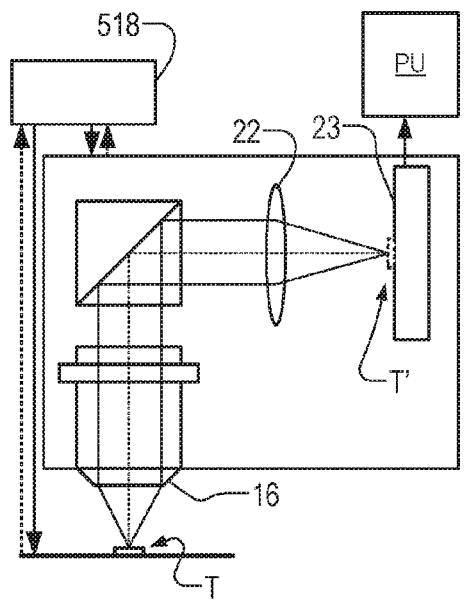
FIGS. 9(a)-9(d) show (a), (b) in the inspection apparatus of FIG. 2 and (c), (d) influence of target motion in the modified apparatus of FIG. 8.
Figure 9B:
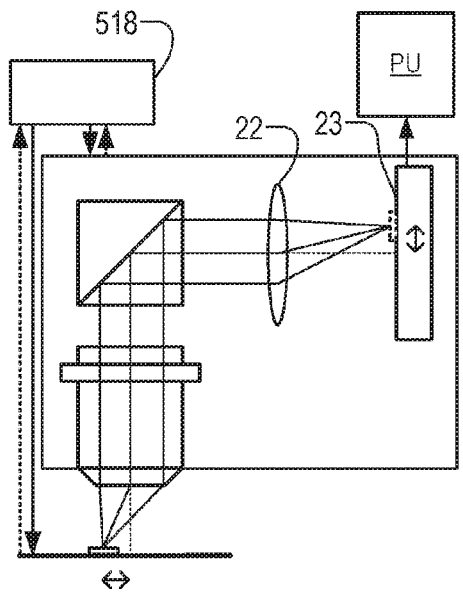

FIGS. 9(a) and 9(b) show the inspection apparatus of FIG. 2 when the apparatus is in use. In FIG. 9(a), a target T is illuminated by the illumination (not shown). The scattered radiation is collected by the objective lens 16 and passes through the optical system. The collected scattered radiation is focused on to the image sensor 23 where it forms an image T' of the target. The position of the image is susceptible to any unintended relative movement between the optical system and the substrate during measurements. In FIG. 9(b), the substrate stage has moved from its initial position (as indicated by the arrow). When target moves relative to the optical system, the image of the target moves accordingly on the sensor 23. It will of course be appreciated that the drawing indicates only one possible direction of relative movement. In reality, the substrate stage and the optical system of the inspection apparatus may move relative to each other in any one of the cardinal directions X, Y or Z (or a combination thereof). Residual movements and vibrations may arise in any of the components, and in any of the directions.

Figure 9C:
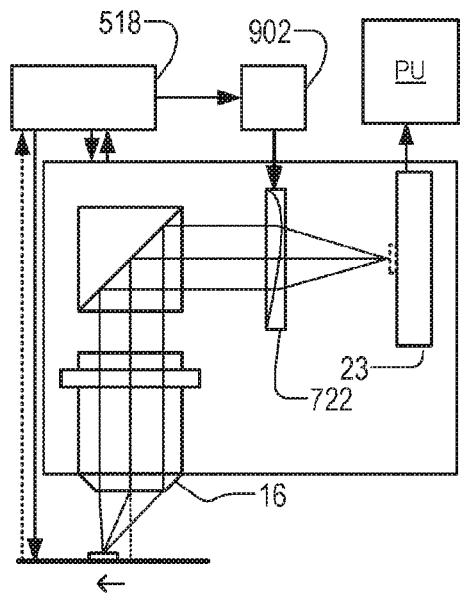
Figure 9D:
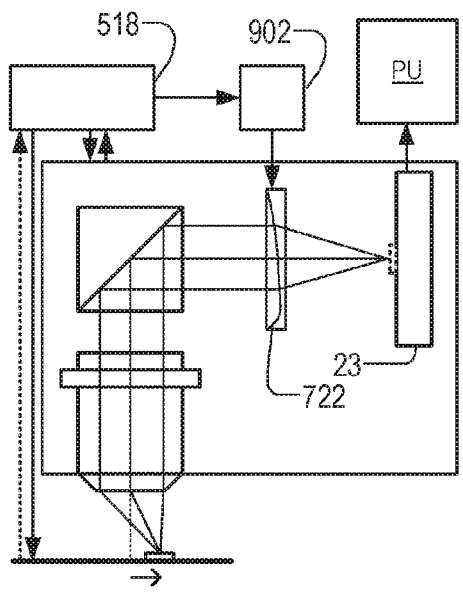

Any movement of the target relative to the optical system during a measurement will degrade the image quality of the images detected by the image detector. Before a suitable image of the target can be taken by the image detector, it is therefore necessary to wait for any relative movement between the substrate stage and the optical system to subside. This increases the time required for performing the measurements. It is therefore desirable to reduce or even remove the settling time, but with heavy components moving at high speed this becomes very difficult to achieve with the required precision FIGS. 9(c) and 9(d) show the same situation but in the modified inspection apparatus of FIG. 8, where the lens 22 has been replaced with a liquid lens 722. A liquid lens controller 902 is provided to set appropriate voltages on the electrodes of the liquid lens 722. In FIG. 9(c), the target has been displaced to one side, and in FIG. 9(d) the target has been displaced in the opposite direction. These directions are, of course, merely exemplary.

The position sensors of the substrate support and the optical system transmit position data to the position controller as before. Position data could, of course, also be obtained in a number of other ways, for example by sensors external to the apparatus (such as a camera system monitoring for any stage movements). The position controller then determines correction information to take into account the relative movement between the substrate stage and the optical system and may issue commands to the actuators to correct the position to a desired stationary value. In the modified apparatus, however, correction information is also sent to the liquid lens controller 902.

When the position controller determines relative movement between the optical system and the substrate stage such that the target T moves from its nominal location, the liquid lens controller is instructed to change the currents of the electrodes of the liquid lens. By changing the currents of the electrodes, the position of the focal point of the liquid lens can be changed to counteract the movement. In this fashion, the position of the image T' of the target on the image sensor 23 can be kept constant.

Referring again to FIG. 6, the liquid lens in the modified inspection apparatus can be controlled to counteract the residual motion 604 to produce a stable image T' before the components have stopped moving. The settling time can be shortened, or even eliminated, by using the liquid lens as described above.

In the present example, controllers 518 and 902 do not merely apply feedback control of the liquid lens, based on measured positions of the optical system and substrate. Rather, a feed-forward control algorithm is implemented, which controls the liquid lens based on prediction of what shape it needs to adopt to correct for positional deviations of the target.

Figure 10:
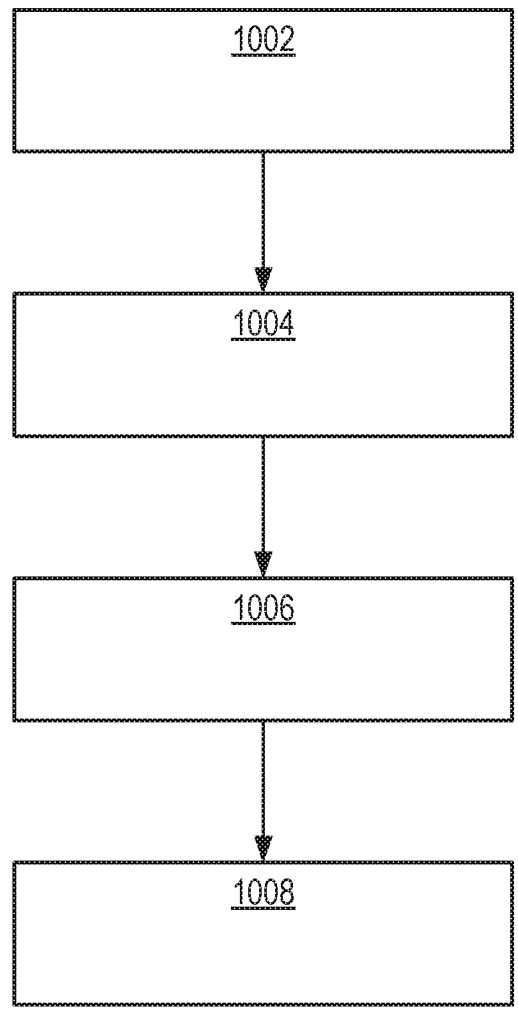
FIG. 10 is a flowchart showing a method of operating the modified inspection apparatus of FIG. 8.

FIG. 10 shows a simple method implementing this feed-forward control. At 1002 position data and/or acceleration data and/or other data is received from sensors associated with one or both of the optical system and the substrate support. At 1004 a prediction is made of relative movement between the optical system and the target, which would normally lead inevitably to movement of the target image T' on sensor 23. At 1006 the prediction of future position or movement is used to calculate corrections to be effected by the liquid lens. At 1008 appropriate electrode voltages or currents are generated to implement the desired corrections and keep the image T' stationary on the sensor 23.

In one example, one or more accelerometers may be provided to allow future trajectories of the components to be predicted. Prediction may be explicitly calculated, or it may be implicit in the functions applied to derive the control signals for the liquid lens. In another example, the prediction and feed-forward control may be based on historical position measurements combined with models of behavior of the affected components. A hybrid technique combining accelerometer measurements and historical position data can be used to predict changes in the position if desired.

As mentioned, prediction can be based on a variety of sensory inputs and/or calculated data. In the case of position data, current and historical positions may be used to make a better prediction than current position alone. Acceleration signals may allow this prediction to be refined further. Predictions may be used that are already implicit in control algorithms for the positioning system itself. For example, a servo control algorithm may (implicitly or explicitly) calculate a prediction of future deviations, in order to generate an actuator command signal that counteracts the deviations. Further, actuator command signals generated already by positioning system controller 518 may be another input to the prediction algorithm.

In a particular example, an accelerometer is fitted to either or both of the optical system or the substrate support. In essence, the accelerometer consists of a force sensor using a fixed mass to detect changes in force or acceleration applied to the mass. In the present example, the fixed mass of the accelerometer is very small, with a corresponding small mass-inertia, when compared to the mass of the components of the optical system or substrate support. The accelerometer will therefore detect a change in force or acceleration on the fixed mass before the position sensors of the optical system or substrate support can detect a position change. The accelerometer sends the data to a calibrated movement model for the optical system or substrate support. The movement model then, based on the data received from the accelerometer, calculates the predicted positions of the optical system and substrate support relative to each other.

Whichever type of sensor and algorithm is used, a single prediction may be produced for the relative position of the optical system and the target T. Alternatively, predictions can be produced separately for the positions of different components (optical system, substrate), and then combined to obtain a correction for the relative position of the substrate and optical system. In addition to the relative movement between the substrate and optical system, there may be relative movement between optical elements within the optical system. It is of course to be noted that the present invention can be used to compensate for such relative movements, in addition to aforementioned compensation for relative movements between substrate and optical system. The positions and corrections may be in one direction only, (for example the Y direction) or may be in multiple directions. Different types of algorithms and sensors can be used to control the liquid lens in different directions, if desired, the required adjustments being combined into a single set of voltages for application to the liquid lens electrodes.

Figure 11:
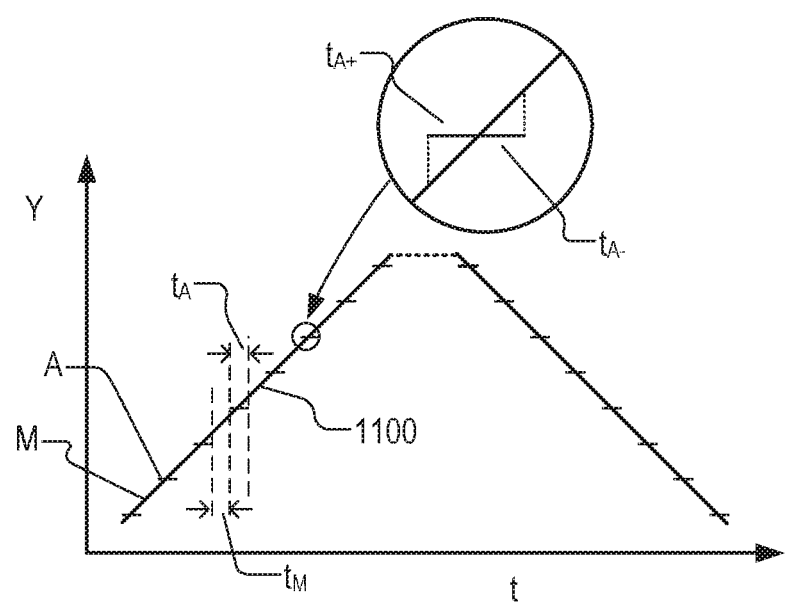
FIG. 11 is a graph showing components of a scanning motion in a further modification of the apparatus of FIG. 8.

Referring to FIGS. 11 and 12, it is possible to modify the control and operation of the modified apparatus of FIG. 8 so that periods of stopping are not required in order to obtain good images. In this modified method of operation, relative movement is deliberately maintained throughout the image acquisition interval tA, while liquid lens 72 is controlled to maintain a stationary image T' of a target on the image sensor 23. In this way, it is also possible to use the liquid lens to enable images of successive targets to be acquired during a continuous scanning operation. Since the movement is not interrupted, actually it can be easier to predict and control the relative position. Because there is no need for sudden acceleration or deceleration of the moving parts, there is also no need for a settlement period since there will be no residual movement to counteract.

Figure 12A:
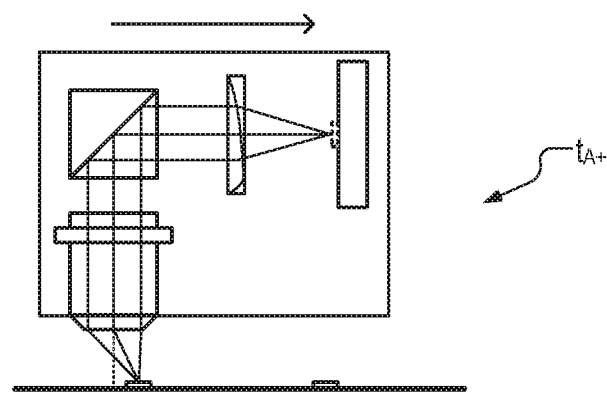
FIGS. 12(a)-12(d) illustrate stages (a) to (d) in the operation of the modified apparatus measuring a first target and moving to a second target.
Figure 12B:
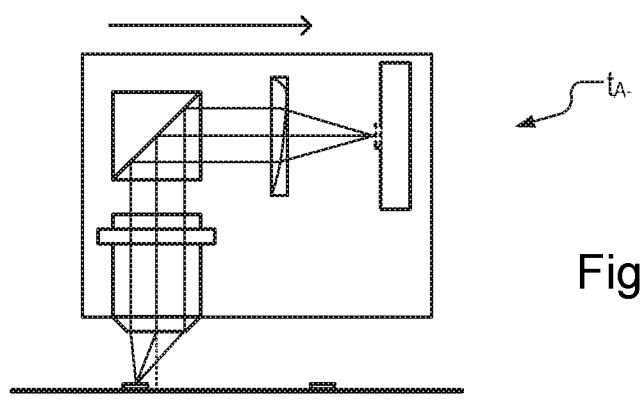

FIG. 11 shows an exemplary movement pattern for imaging targets during a continuous scan operation. The graph 1100 indicates a continuous, constant-velocity motion of the optical system relative to the substrate. Different targets come within a field of view of the optical system along the trajectory. The time is divided into movement intervals tM and acquisition intervals tA. FIG. 12 shows a side view of the scanning process in one example. In the present example, we can assume for simplicity that the optical system moves in the Y-direction and the substrate stage is kept stationary. The substrate can be move in the X direction during the movement intervals tM, however, or even during the acquisition interval also. Once a particular target area is safely within a field of view of the optical system, it then comes within a correction range of the liquid lens (which may be the entire field of view or a subset of it)/The focal point of the liquid lens is moved so as to produce an target image T' centered on the sensor 23. This initial condition is shown in FIG. 12(a). As relative motion continues, the image of the target can be kept in a constant location on the image detector until the target moves out of the correction range of the liquid lens at (b). While the target is within the correction range of the liquid lens, the target image on the image detector will not move.

During this period, an image of the target can be acquired without the quality of the image being adversely affected by movement. In other words, the image detector is able to acquire an image of the target area, but without having to stop the scanning motion of the optical system.

As seen in the inset detail in FIG. 11, the acquisition interval tA can be divided notionally into a "liquid lens ahead" interval tA+ and a "liquid lens behind" interval tA−.

The transition between these intervals is not a distinct step, but merely occurs when the liquid lens passes through its neutral state (FIG. 8 (b)).

Figure 12C:
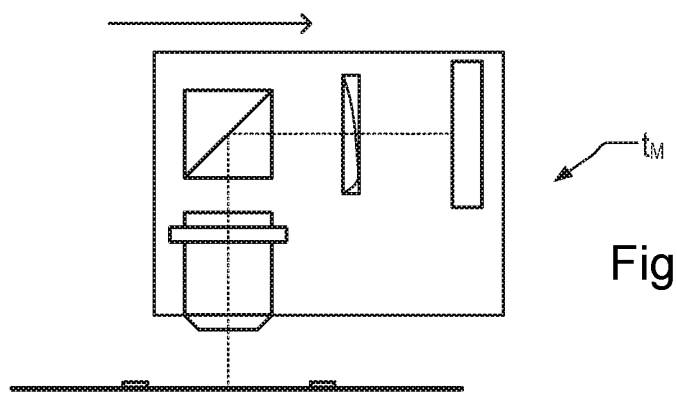
Figure 12D:
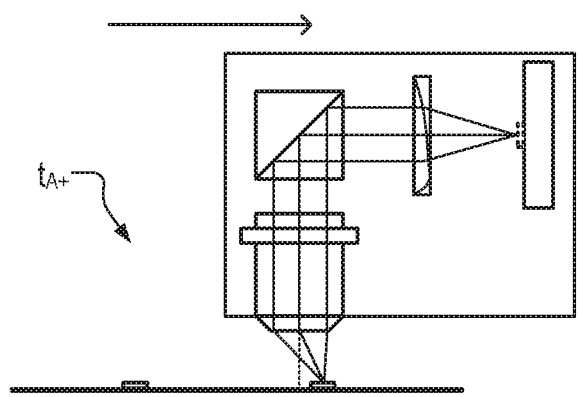

Once the image has been acquired, the liquid lens is reset during the next movement interval tM (as shown in FIG. 12(c)). Once the next target enters the field of view and the correction range of the liquid lens, the focal point of the liquid lens is moved onto the next target. At (d), we see the acquisition of the next target image beginning with a "liquid lens ahead" interval tA+. This process can continue for as long as applicable.

As mentioned, one advantage of the continuous scanning method is that residual motion may be less than in the case of stop-start motion. In any case, additional corrections can be fed to the liquid lens controller to correct for deviations from the ideal trajectory. These deviations may be longitudinal and/or transverse to the direction of scanning. Note also that the position of the target image on the image sensor 23 may or may not be exactly centered on some nominal position. Provided that it is within the field of view and correction range throughout the acquisition interval, and the velocity of the relative movement is well known, the liquid lens will keep the image T' at one stationary position on the image sensor 23. If necessary, image processing algorithms can be applied to find exactly a region of interest (ROI) in each acquired image.

While the example described above have included (i) stop-start movements with correction of residual movements and (ii) continuous velocity scanning (ii), these are not the only modes of operation contemplated. The movement that is easiest to follow is a constant speed but so long as there is a predictable vibration with a known shape, we can use a feed-forward system to follow and correct it.

Further, a trajectory with repeating speed differences can be envisaged that uses a slower but very controlled speed for image acquisitions and uses a maximum move speed between the targets will also work. This can be useful where the sensor integration time required is too long for the target to remain within the correction range for long enough, at the full movement speed.

It is also noted that the scanning methods (whether constant speed or slow speed) can bring an extra advantage in measurement quality. As mentioned already in relation to FIG. 4, different optical paths in the optical system may bring slightly different aberrations, so that a measurement using one optical path may be slightly different than a measurement using another optical path, even though the measured structure is the same. These different paths may be in the illumination path IP and/or in the collection & imaging path CP. In the scanning methods disclosed herein, using a liquid lens to maintain a stationary image of the target on the sensor 23, no single set of optical paths is used in a given measurement. Rather, the resulting image is the result of averaging of the lens/sensor aberration over a number of paths, and the measurements become more reliable as a result.

Figure 13:
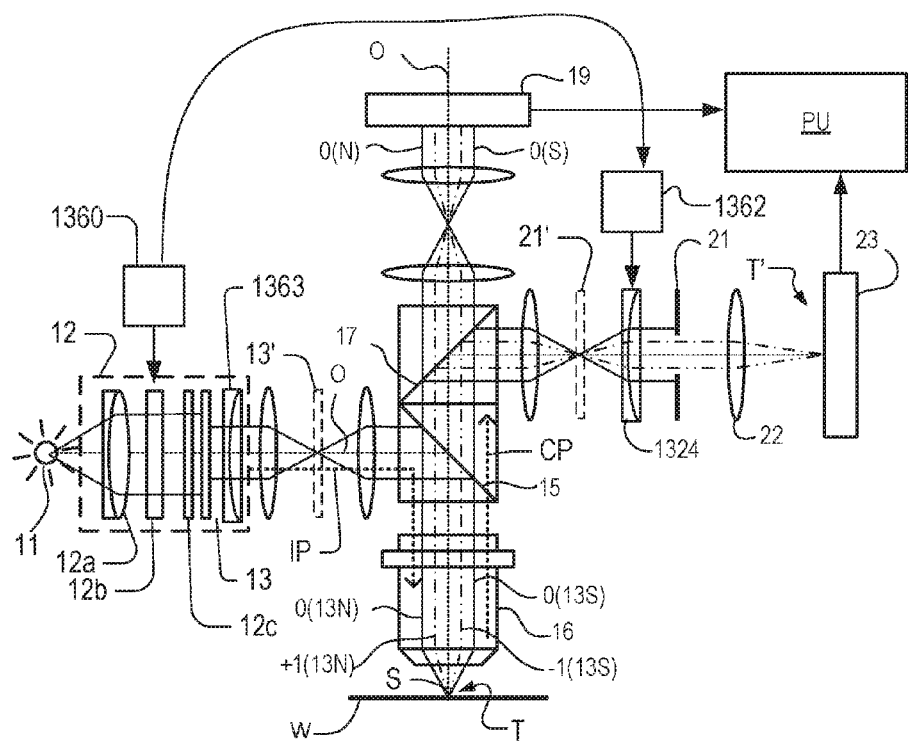
FIG. 13 shows a second modified inspection apparatus incorporating another liquid lens in the imaging optical system.

FIG. 13 shows an inspection apparatus modified in accordance with a second aspect of the present disclosure. The inspection apparatus is identical to that shown in FIG. 2, except that lens 24 has been replaced with a liquid lens 1324. In the present aspect, the liquid lens is used for reducing the effects of chromatic aberration induced by the remaining optical components of the imaging optical system, as will be explained in more detail in the following.

Figure 14A:
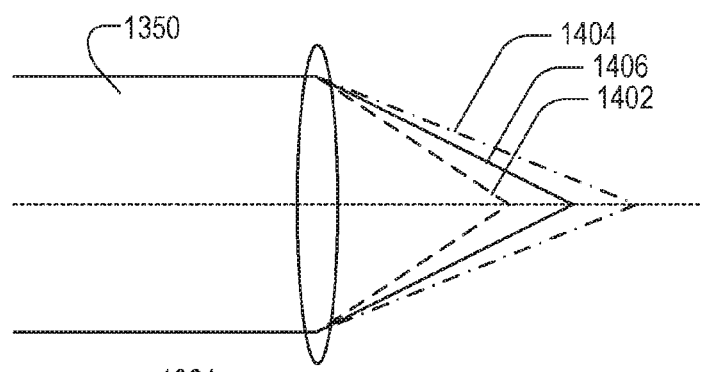
FIGS. 14(a) and 14(b) illustrate the focusing of radiation of different wavelengths in the imaging optical system of (a) the apparatus of FIG. 2 and (b) the apparatus of FIG. 13.

A second liquid lens 1363 can additionally or alternatively be inserted into illumination system 12. The second liquid lens can be used to reduce the effects of chromatic aberration in the illumination system. This allows for the illumination spot to be formed on the target consistently at different wavelengths, which increases the overall accuracy of the metrology system. FIG. 14(a) illustrates the principle of chromatic aberration, as it affects the focusing of an image such as on image sensor 23. A light beam 1350 is incident on a lens. The incoming light is refracted by the lens in a well-known manner. Due to the dispersion of the material of the lens, the focal length of the lens depends on the wavelength of the transmitted light. Generally, the focal length of a simple refractive lens is proportional to the wavelength of incoming light. Inspection apparatuses typically use a number of wavelengths, albeit one at a time, when performing measurement. In the present example, the incoming light beam has one of three specific wavelengths. It is, in principle, also possible to use polychromatic light in some instances. As can be seen in FIG. 14(a), the light component with the shortest wavelength 1402 has the shortest effective focal length, and the light component with the longest wavelength 1404 has the longest effective focal length. The effective focal length of the component with the middle wavelength 1406 lies between the other two focal lengths. The lens cannot be in focus simultaneously for all three wavelengths.

Figure 14B:
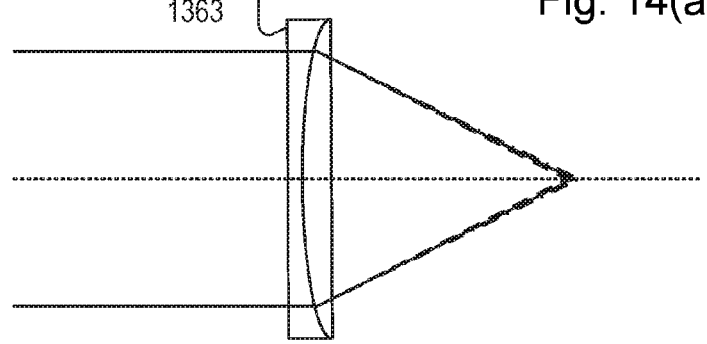

FIG. 14(b) illustrates the use of a liquid lens 1324, 1363 to counteract the effects of chromatic aberration in the apparatus of FIG. 13. As explained previously, the focal length of the liquid lens can be adjusted by increasing or decreasing the voltage of the electrodes of the liquid lens, thereby increasing or decreasing the curvature of the surface between the first and second liquids of the lens. If the wavelength of the incoming light is known, it is possible to precisely adjust the focal length of the lens while taking into account the effect of wavelength of the focal length. As can be seen, all three wavelengths are focused to the same focal point.

Referring again to FIG. 13 light source 11 emits light, which passes through a color filter 12b (other wavelength selection mechanism are possible). The color filter, for example comprising a color wheel or graduated filter, is controlled by a controller 1360. This enables the selection of light with different colors (more generally, radiation of different visible and non-visible wavelengths). The filtered light is delivered to, and scattered by, a target area on a target substrate as described above. In the imaging optical system, the focal length of liquid lens 1324 is controllable by a controller 1362. In the illumination system, the focal length of liquid lens 1363 is controllable by a controller 1362. The liquid lenses 1324 and 1363 are shown at particular locations in the optical system but similar effects can be used with liquid lens at other locations. The liquid lens may replace a fixed lens, or be additional to it.

As described with reference to FIG. 14, light with different wavelengths will be refracted differently by the various optical components of the optical system. In the present example, chromatic aberration is only illustrated with respect to lens 24. However, it should be noted that each diffractive optical component of the optical system adds to effect. Hence, the chromatic aberration of the entire optical system is the sum of chromatic aberration induced by each optical component. If left uncorrected, the chromatic aberration of the optical system can significantly affect the image quality of the images acquired by the image detector, except perhaps at one specific wavelength.

Figure 15:
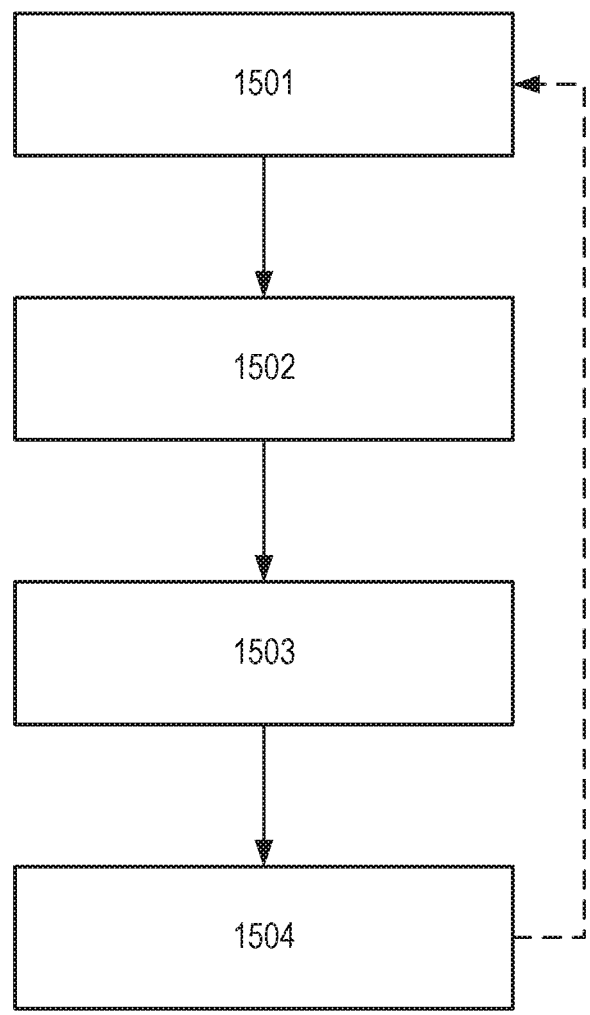
FIG. 15 is a flowchart showing a method of operating the second modified inspection apparatus of FIG. 13.

The method for removing chromatic aberration will now be described with reference to FIGS. 13 and 15. A wavelength to be used for a measurement is selected at 1501 by the controller 1360. The selected can either be performed automatically as part of a pre-defined program (metrology recipe), or it can be selected manually by an operator. The control unit transmits data to the color filter 12b in the normal way. Additionally, the control unit transmits 1502 data relating to the selected wavelength to the liquid lens controller 1362. This in turn applies signals to the individual electrodes of the liquid lens, so that the liquid lens can compensate 1503 (at least partially) for chromatic aberration not only in itself, but also in other elements of the imaging optical system. This ensures that the image of the target is correctly focused onto the image detector regardless of the wavelength of the light used for any given measurement. The image detector then acquires 1504 an image of the target. It will be understood that the liquid lens controller 1362 can be commanded directly by a central controller and/or by manual command, rather than via color controller 1360. The central controller or manual operator is then responsible for synchronizing the changes of wavelength with appropriate settings of the liquid lens.

The various aspects of the disclosure as described above and illustrated in the drawings can be used individually or in combination. In other words, an inspection apparatus according to the present disclosure may include a liquid lens controlled to maintain a stationary target image in the presence of relative movement and/or a liquid lens controlled to correct for chromatic aberrations when working at different wavelengths and/or to provide both spot illumination and field illumination from a single illumination optical system. The same or another liquid lens or lenses can apply other corrections and changes in the set-up and maintenance of the apparatus over time.

Figure 16:
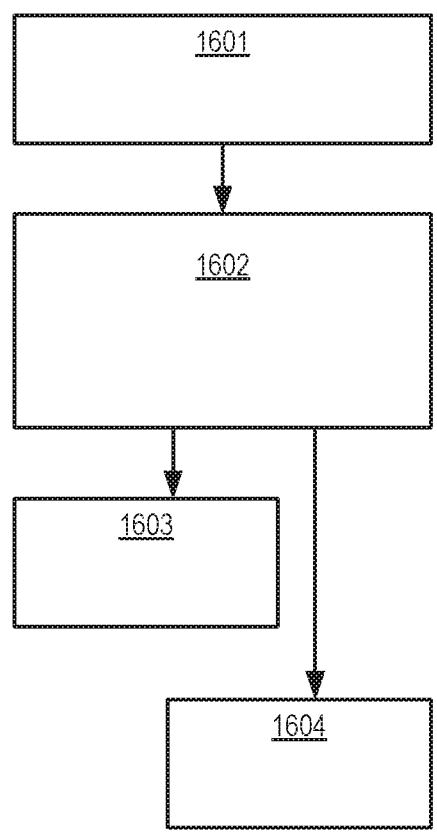
FIG. 16 is a flow chart illustrating a method of controlling performance of a metrology method and/or of a lithographic manufacturing process using measurements made using the inspection apparatus of FIGS. 8 and/or 13.

FIG. 16 illustrates the application of a measurement method using any or all of the modified inspection apparatuses and methods of the present disclosure, in the management of a lithographic manufacturing system. The steps will be listed here, and then explained in more detail:

1601: Process wafer to produce structures on substrate
1602: Measure CD and/or other parameter across substrate
1603: Update metrology recipe
1604: Update lithography and/or process recipe At step 1601, structures are produced across a substrate using the lithographic manufacturing system. At 1602, the metrology apparatus 240, made and operated according to one or more aspects of the present disclosure is used (optionally in combination with other metrology apparatus and information sources) to measure a property of the structures across the substrate. At step 1703, optionally, metrology recipes and calibrations of the metrology apparatus and/or other metrology apparatuses are updated in light of the measurement results obtained.

At step 1604, measurements of CD or other parameters are compared with desired values, and used to update settings of the lithographic apparatus and/or other apparatus within the lithographic manufacturing system. By providing an inspection apparatus with improved throughput and/or accuracy, using the modifications and methods described, the performance of the whole manufacturing system can be improved.

In the above steps, it is assumed that sufficient targets are measured across a substrate and across multiple substrates, that statistically reliable models of the process are derivable. The profile of CD and other parameters does not need to be expressed entirely as a variation across the substrate. It can be expressed for example as an intra-field profile that is common to all fields (each instance of patterning using the patterning device MA at a different location on the substrate W) and a lower order, inter-field, variation onto which the intra-field variation is repeatedly superimposed. The settings of the lithographic process adjusted in step 1604 can include intra-field settings as well as inter-field settings. They may be applicable to all operations of the apparatus, or specific to a particular product layer.

CONCLUSION

A method of manufacturing devices using the lithographic process can be improved by providing an inspection apparatus as disclosed herein, using it to measure processed substrates to measure parameters of performance of the lithographic process, and adjusting parameters of the process to improve or maintain performance of the lithographic process for the processing of subsequent substrates.

While the target structures described above are metrology targets specifically designed and formed for the purposes of measurement, in other embodiments, properties may be measured on targets which are functional parts of devices formed on the substrate.

While the first and second aspects of the disclosure are discussed above in the context of a metrology apparatus 240 inspecting substrates after a lithographic patterning operation, they may be applied also prior to the lithographic patterning operation. In this regard, the term "inspection apparatus" should be understood to include position sensors such as the alignment sensors and level sensors of the lithographic apparatus 100 itself. Measurement of properties of target structures as described herein should be taken to include measurement of the position of the target structure relative to some reference frame, and not only inherent properties such as CD and overlay. The target structure may be for example an alignment mark formed on the substrate prior to a patterning operation. The image sensor need not be a multi-pixels image sensor in that case.

An implementation of the present disclosure in one or more of its various aspects may include a computer program containing one or more sequences of machine-readable instructions describing methods of controlling the liquid lens(es) and other components to perform the operations described above. This computer program may be executed for example in a separate computer system employed for the control of the liquid lens alone. Alternatively, the liquid lens control method may be wholly or partly performed within a general controller of the positioning system of the apparatus. The controller may be integrated within processing unit PU in the apparatus of FIG. 2, 8 or 13 and/or the control unit LACU of FIG. 1. There may also be provided a data storage medium (e.g., semiconductor memory, magnetic or optical disk) having such a computer program stored therein.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further embodiments according to the current invention are provided in below numbered clauses:

1. An inspection apparatus for measuring properties of a target structure on a substrate, the apparatus comprising:
   a substrate support for supporting the substrate;
   an optical system for illuminating the target structure with radiation and collecting diffracted radiation from the target structure, the optical system comprising imaging optics and an image sensor; and
   a positioning system for causing movements of one or both of the optical system and the substrate support so as to position an individual target structure relative to the optical system so that the imaging optics can use a portion of the diffracted radiation to form an image of the target structure on the image sensor during an image acquisition interval,
   wherein the imaging optics includes a liquid lens and a controller, the controller being operable to control the liquid lens to maintain said image stationary during said image acquisition interval while allowing for relative movement between the optical system and the target structure.

2. An inspection apparatus according to clause 1, wherein the controller is arranged to receive positioning information from the positioning system to implement a feed-forward control of the liquid lens.

3. An inspection apparatus according to clause 2, wherein the positioning information from the positioning system is based on measurements of acceleration from one or more acceleration sensors.

4. An inspection apparatus according to clause 2 or 3, wherein the positioning information from the positioning system comprises predictions of position from a positioning system controller.

5. An inspection apparatus according to any previous clause, wherein the positioning system is arranged to maintain the target structure and the optical system in a fixed relative position during said image acquisition interval, the liquid lens controller being operable to compensate residual movements.

6. An inspection apparatus according to any of clauses 1 to 4, wherein the positioning system is arranged to maintain the target structure and the optical system in a relative scanning movement during said image acquisition interval.

7. An inspection apparatus according to any previous clause, wherein the positioning system comprises a substrate positioning subsystem arranged to move the substrate support in at least a first direction and an optical system positioning subsystem arranged to move the optical system in at least a second direction, the positioning system thereby implementing relative movement between the optical system and the substrate in two dimensions.

8. An inspection apparatus according to any previous clause, wherein the liquid lens is a multi-pole liquid lens.

9. An inspection apparatus for measuring properties of a target structure on a substrate, the apparatus comprising:
   an optical system for illuminating a target structure with radiation and collecting diffracted radiation from the target structure, the optical system including illumination optics, imaging optics and an image sensor, the imaging optics using a portion of the diffracted radiation to form an image of the target structure on the image sensor;
   wherein the optical system is arranged to illuminate the target structure and form an image while selecting a wavelength range of said radiation, and wherein the optical system comprises at least one liquid lens and a controller, the controller being operable to control the liquid lens to compensate for chromatic aberration of the optical system according to the selected wavelength range.

10. An inspection apparatus according to clause 9, wherein the optical system is arranged automatically to illuminate a target structure and form images sequentially with different wavelength ranges, the controller controlling the liquid lens automatically to compensate for chromatic aberration for each selected wavelength range.

11. An inspection apparatus according to clause 9 or 10, wherein the controller is arranged to control a focal length of the liquid lens according to the selected wavelength range.

12. An inspection apparatus according to any of clauses 9 to 11, wherein at least one liquid lens is comprised in the illumination optics of the optical system.

13. An inspection apparatus according to any of clauses 9 to 12, wherein at least one liquid lens is comprised in the imaging optics of the optical system.

14. A method of operating an optical system comprising:
   providing a substrate support for supporting a substrate;
   providing an optical system for illuminating the target structure with radiation and collecting diffracted radiation from the target structure;
   causing movements of one or both of the optical system and the substrate support so as to position an individual target structure on a substrate relative to the optical system;
   causing imaging optics within the optical system to use a portion of the diffracted radiation to form an image of the target structure on the image sensor during an image acquisition interval,
   wherein the imaging optics includes a liquid lens, the method further comprising controlling the liquid lens to maintain said image stationary during said image acquisition interval while allowing for relative movement between the optical system and the target structure.

15. A method according to clause 14, wherein the controlling step comprises a feed-forward control of the liquid lens.

16. A method according to clause 15 wherein said feed-forward control is based on measurements of acceleration from one or more acceleration sensors.

17 A method according to clause 15 or 16 wherein said feed-forward control includes predicting variations in relative position between the optical system and the target structure.

18. A method according to any of clauses 14 to 17 wherein the step of causing movements comprises moving the optical system to a target structure and then maintaining the target structure and the optical system in a fixed relative position during said image acquisition interval, and the controlling step comprises controlling the liquid lens to compensate residual movements.

19. A method according to any of clause 14 to 17 wherein the step of causing movements comprises moving the optical system to a target structure and maintaining the target structure and the optical system in a relative scanning movement throughout said image acquisition interval, and the controlling step comprises controlling the liquid lens during the acquisition interval to compensate the relative scanning movement.

20. A method according to any of clauses 14 to 19 where the step of causing movements comprises moving the substrate support in at least a first direction and moving the optical system in at least a second direction, thereby implementing relative movement between the optical system and the substrate in two dimensions.

21. A computer program product comprising machine-readable instructions for causing a programmable controller to act as the liquid lens controller in an apparatus according to any of clauses 1 to 13.

22. A computer program product comprising machine-readable instructions for causing a programmable controller to control a liquid lens to implement a method according to any of clauses 14 to 20.

23. A method of operating an optical system for measuring properties of a target structure on a substrate, the method comprising:
providing an optical system including illumination optics, imaging optics and an image sensor;
using the illumination optics to illuminate the target structure with radiation of a selected wavelength range;
collecting diffracted radiation from the target structure; and
using the imaging optics to form an image of the target structure on the image sensor using at least a portion of the collected diffracted radiation;
wherein the optical system comprises at least one liquid lens the method including controlling the liquid lens automatically to compensate for chromatic aberration of the optical system according to the selected wavelength range.

24. A method according to clause 23 wherein the illumination optics is used to illuminate a target structure sequentially with different wavelength ranges, liquid lens being controlled automatically to compensate for chromatic aberration for each selected wavelength range.

25. A method according to clause 23 or 24 wherein a focal length of the liquid lens is controlled according to the selected wavelength range.

26. A method according to clause 23, 24 or 25 wherein at least one liquid lens is controlled so as to maintain focus of a spot of radiation in the illuminating step.

27. A method according to clause 23, 24, 25 or 26 wherein at least one liquid lens is controlled to maintain focus of the image on the image sensor.

28. A computer program product comprising machine-readable instructions for causing a programmable controller to act as the liquid lens controller in an apparatus according to any of clauses 9 to 13.

29. A computer program product comprising machine-readable instructions for causing a programmable controller to control a liquid lens to implement a method according to any of clauses 23 to 27.

30. A device manufacturing method comprising:
transferring a pattern from a patterning device onto a substrate using a lithographic process, the pattern defining at least one periodic structure;
measuring one or more properties of the periodic structure to determine a value for one or more parameters of the lithographic process; and
applying a correction in subsequent operations of the lithographic process in accordance with the measured property,
wherein the step of measuring the properties of the periodic structure includes measuring a property using an apparatus according to any of clauses 1 to 13.

31. A device manufacturing method comprising:
transferring a pattern from a patterning device onto a substrate using a lithographic process, the pattern defining at least one periodic structure;
measuring one or more properties of the periodic structure to determine a value for one or more parameters of the lithographic process; and
applying a correction in subsequent operations of the lithographic process in accordance with the measured property,
wherein the step of measuring the properties of the periodic structure includes measuring a property by a method according to any of clauses 14 to 20 and 23 to 29.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An inspection apparatus for measuring properties of a target structure on a substrate, the apparatus comprising:
a substrate support configured to support the substrate;
an optical system configured to illuminate the target structure with radiation and collect diffracted radiation from the target structure, the optical system comprising imaging optics and an image sensor, the imaging optics comprising a liquid lens and a controller; and
a positioning system configured to move one or both of the optical system and the substrate support so as to position an individual target structure relative to the optical system so that the imaging optics uses a portion of the diffracted radiation to form an image of the target structure on the image sensor during an image acquisition interval,
wherein the controller is configured to receive a feedback signal and a feed-forward predictive signal, the feed-forward predictive signal being based on a sensor or calculation, that are used by the controller to control the liquid lens to compensate for residual movement to keep the image stationary during the image acquisition interval while also allowing for relative movement between the optical system and the target structure during the image acquisition.

2. The inspection apparatus according to claim 1, wherein the controller is arranged to receive positioning information from the positioning system to implement the feed-forward control of the liquid lens.

3. The inspection apparatus according to claim 2, wherein the positioning information from the positioning system is based on measurements of acceleration from one or more acceleration sensors.

4. The inspection apparatus according to claim 2, wherein the positioning information from the positioning system comprises predictions of position from a positioning system controller.

5. The inspection apparatus according to claim 1, wherein the positioning system comprises a substrate positioning subsystem arranged to move the substrate support in at least a first direction and an optical system positioning subsystem arranged to move the optical system in at least a second direction, the positioning system thereby implementing relative movement between the optical system and the substrate in two dimensions.

6. The inspection apparatus according to claim 1, wherein the liquid lens is a multi-pole liquid lens.

7. A method of operating an optical system comprising:
illuminating a target structure on a substrate with radiation;
collecting diffracted radiation from the target structure;
positioning the target structure relative to the optical system;
forming an image of the target structure using the diffracted radiation on an image sensor during an image acquisition interval;
determining feedback information with regard to relative movement between the optical system and the target structure;
determining feed-forward predictive information relative to predicted future movement between the optical system and the target structure, the feed-forward predictive information being either measured or calculated; and
controlling a liquid lens based on the feedback and feed-forward predictive information to maintain the image stationary during the image acquisition interval while allowing for relative movement between the optical system and the target structure.

8. The method as claimed in claim 7, wherein the feed-forward information is based on measurements of acceleration from one or more acceleration sensors.

9. The method as claimed in claim 7, wherein the feed-forward information includes predicting variations in relative position between the optical system and the target structure.

10. The method as claimed in claim 7, wherein:
the positioning comprises moving the optical system to a target structure and then maintaining the target structure and the optical system in a fixed relative position during said image acquisition interval, and
the controlling comprises controlling the liquid lens to compensate residual movements.

11. A method comprising:
illuminating a target structure on a substrate with radiation;
collecting diffracted radiation from the target structure;
positioning the target structure relative to the optical system;
forming an image of the target structure using the diffracted radiation on an image sensor during an image acquisition interval; and
using a non-transient computer readable medium comprising machine-readable instructions to:
determine feedback information with regard to relative movement between the optical system and the target structure;
determine feed-forward predictive information relative to predicted future movement between the optical system and the target structure, the feed-forward predictive information being either measured or calculated; and
cause a liquid lens controller to perform operations comprising controlling a liquid lens to maintain said image stationary during the image acquisition interval while allowing for relative movement between the optical system and the target structure based on the feedback and feed-forward predictive information.

12. A device manufacturing method comprising:
transferring a pattern from a patterning device onto a substrate using a lithographic process, the pattern defining at least one periodic structure;
continuously measuring one or more properties of the periodic structure to determine a value for one or more parameters of the lithographic process during the transferring; and
continuously applying a correction in subsequent operations of the lithographic process in accordance with the measured property,
wherein the continuously measuring the properties of the periodic structure includes measuring a property using an apparatus comprising:
a substrate support configured to support the substrate;
an optical system configured to illuminate the target structure with radiation and collect diffracted radiation from the target structure, the optical system comprising imaging optics and an image sensor, and the imaging optics comprising a liquid lens and a controller; and
a positioning system configured to continuously move one or both of the optical system and the substrate support so as to position an individual target structure relative to the optical system so that the imaging optics uses a portion of the diffracted radiation to form an image of the target structure on the image sensor continuously during an image acquisition interval and the transferring,
wherein the controller is configured to continuously receive a feedback signal and a feed-forward predictive signal, the feed-forward predictive signal being based on a sensor or calculation, that are used by the controller to control the liquid lens to compensate for residual movement to continuously keep the image stationary during the image acquisition interval and the transferring while also continuously allowing for relative movement between the optical system and the target structure during the image acquisition and transferring.

* * * * *